United States Patent
Deppermann

(10) Patent No.: US 7,454,989 B2
(45) Date of Patent: Nov. 25, 2008

(54) SEED CORING SYSTEM AND METHOD FOR ARRANGING SEED CORES FOR ANALYSIS

(75) Inventor: Kevin L. Deppermann, St. Charles, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 11/594,099

(22) Filed: Nov. 7, 2006

(65) Prior Publication Data

US 2007/0068285 A1    Mar. 29, 2007

Related U.S. Application Data

(62) Division of application No. 11/216,382, filed on Aug. 31, 2005, now Pat. No. 7,134,351, which is a division of application No. 10/444,939, filed on May 21, 2003, now Pat. No. 6,959,617.

(60) Provisional application No. 60/383,560, filed on May 24, 2002.

(51) Int. Cl.
*G01N 1/08* (2006.01)

(52) U.S. Cl. .................................. 73/864.45

(58) Field of Classification Search . 73/864.44–864.45; 99/547, 551, 552
See application file for complete search history.

(56) References Cited

U.S. PATENT DOCUMENTS

| 2,382,961 | A | * | 8/1945 | Coons | 99/548 |
| 2,611,434 | A | * | 9/1952 | Mugler | 83/171 |
| 2,740,440 | A | | 4/1956 | Wright | |
| 3,211,201 | A | * | 10/1965 | Creed | 99/543 |
| 3,373,786 | A | * | 3/1968 | Anderson et al. | 99/490 |
| 3,586,081 | A | | 6/1971 | Loveland et al. | |
| 4,252,056 | A | * | 2/1981 | Altman | 99/551 |
| 4,337,693 | A | * | 7/1982 | Dandrea | 99/491 |
| 4,453,458 | A | * | 6/1984 | Altman | 99/544 |
| 4,530,278 | A | | 7/1985 | Sarig et al. | |
| 4,638,867 | A | | 1/1987 | Hansen et al. | |
| 5,181,457 | A | | 1/1993 | Toshiyuki | |
| 5,541,968 | A | | 7/1996 | Brassel | |

(Continued)

FOREIGN PATENT DOCUMENTS

DE    4215964  A  * 11/1992

(Continued)

*Primary Examiner*—Hezron Williams
*Assistant Examiner*—Nashmiya S Fayyaz
(74) *Attorney, Agent, or Firm*—James E. Davis; Jospeh A. Schaper; Harness, Dickey & Pierce, P.L.C.

(57) ABSTRACT

A coring device includes a base portion that receives an arrayed plurality of samples, the base portion including a plurality of vertically oriented slider rods. A coring portion including an arrayed plurality of samples is slidable along the vertically oriented slider rods between a retracted position and an actuated position where cores are taken from the samples. An extraction portion including arrayed plurality of extraction pins aligned with the arrayed plurality of coring tubes for insertion therein is also slidable along the vertically oriented slider rods between a retracted position and an actuated position where the extraction pins eject cores from the coring tubes. A coring drive mechanism is provided to mechanically move the coring portion between the retracted position and the actuated position.

4 Claims, 5 Drawing Sheets

U.S. PATENT DOCUMENTS

| | | |
|---|---|---|
| 5,577,439 A | 11/1996 | Cimperman et al. |
| 5,590,591 A | 1/1997 | Kim |
| 5,870,949 A | 2/1999 | Cimperman et al. |

FOREIGN PATENT DOCUMENTS

| | | | |
|---|---|---|---|
| DE | 4215964 A1 | 11/1992 | |
| JP | 03047060 A | * | 2/1991 |
| JP | 08 080181 A | | 3/1996 |
| WO | WO 99/44063 | | 9/1999 |

* cited by examiner

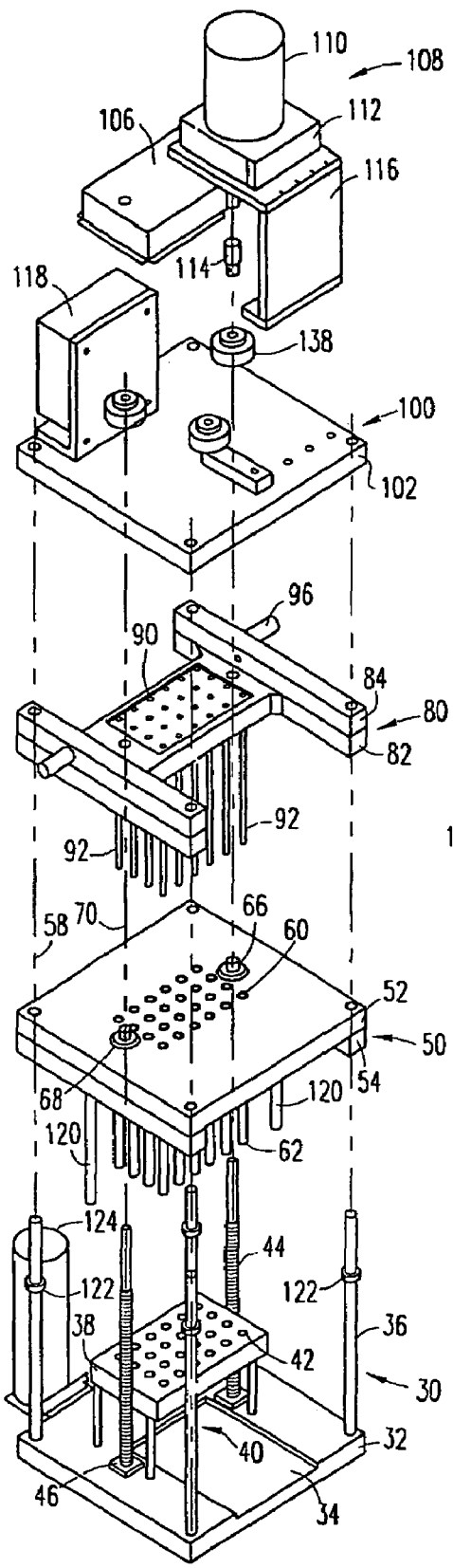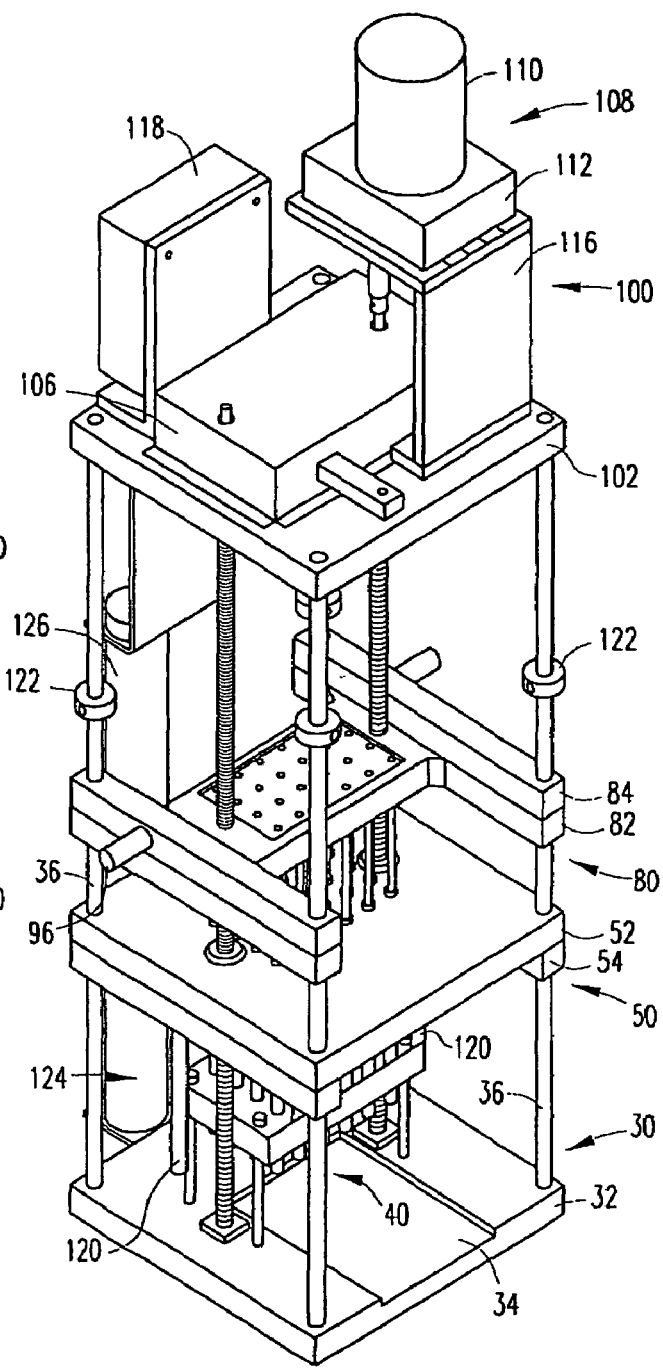
FIG. 12
FIG. 13

SEED CORING SYSTEM AND METHOD FOR ARRANGING SEED CORES FOR ANALYSIS

CROSS-REFERENCE TO RELATED APPLICATIONS

This application is a divisional of U.S. patent application Ser. No. 11/216,382, filed Aug. 31, 2005, now U.S. Pat. No. 7,134,351 which is a divisional of U.S. patent application Ser. No. 10/444,939, filed May 21, 2003 (now U.S. Pat. No. 6,959,617), which claims domestic priority from U.S. Provisional Application Ser. No. 60/383,560, filed May 24, 2002. The entire disclosures of U.S. patent application Ser. No. 11/216,382, U.S. patent application Ser. No. 10/444,939 and U.S. Provisional Application Ser. No. 60/383,560 are hereby incorporated herein by reference.

BACKGROUND OF THE INVENTION

The present invention relates to the coring of agricultural products, more specifically, seeds (and even more particularly, soybeans), for research and analysis.

Agricultural product testing, research, analysis and breeding requires the production and handling of a large number of samples. Take, for example, research and development efforts concerning the breeding of improved varieties of seeds, such as, soybeans. Careful analysis of the seeds, and more specifically, the cores, germs and/or endosperms of such seeds (i.e., the samples), is critical to the detection of traits of interest and the efforts to screen seeds for the presence of these traits and effectuate the propagation of desired traits through selective breeding in subsequent generations.

A number of destructive techniques are known in the art for obtaining these samples for analysis. Dissection is one well known method for separating germ from endosperm. Coring is another well known method for recovering a seed core for analysis. Each of these methods is, however, generally manually implemented at great expense of manpower resources, money and time. This, accordingly, significantly adds to the cost of sample analysis and delays its completion. This is especially frustrating in agricultural product breeding programs where the monetary issues significantly raise the overall cost of breeding new seed lines and the time issues can significantly delay the selection process and production of each new generation.

A need therefore exists for an automated technique for producing agricultural samples from seeds. More specifically, a need exists for an automated technique for obtaining cores from seeds, such as, soybeans. Still further, a need exists for a method of more efficiently handling cores for analysis.

SUMMARY OF THE INVENTION

The present invention is directed to a coring system. The coring system includes a coring plate having an arrayed plurality of openings into which are mounted a plurality of coring tubes. A mechanical drive mechanism is operable to translate the coring plate between a retracted position and an activated position. When translated toward the activated position, the plurality of coring tubes act to core a correspondingly arrayed plurality of objects (such as, for example, seeds).

The coring system may further include an extraction plate having an arrayed plurality of openings aligned with the arrayed plurality of openings in the coring plate, the extraction openings mounting a plurality of extraction pins positioned for insertion within an opening of a corresponding coring tube. Translation of the extraction plate from a retracted position toward an activated position causes the extraction pins to eject cores from the coring tubes.

In accordance with an embodiment of the invention, a coring device includes a base portion that receives an arrayed plurality of samples, the base portion having a plurality of vertically oriented slider rods. A coring portion including an arrayed plurality of coring tubes aligned with the arrayed plurality of samples is slidable along the vertically oriented slider rods between a retracted position and an actuated position where cores are taken from the samples. An extraction portion including an arrayed plurality of extraction pins aligned with the arrayed plurality of coring tubes for insertion therein is also slidable along the vertically oriented slider rods between a retracted position and an actuated position where the extraction pins eject cores from the coring tubes. A drive mechanism is provided to mechanically move the coring portion between the retracted position and the actuated position.

BRIEF DESCRIPTION OF THE DRAWINGS

A more complete understanding of the method and apparatus of the present invention may be acquired by reference to the following Detailed Description when taken in conjunction with the accompanying Drawings wherein:

FIG. 12 is an exploded orthogonal view of the coring system of the present invention;

FIG. 13 is an assembled orthogonal view of the coring system of the present invention;

DETAILED DESCRIPTION OF THE DRAWINGS

Figure 1:
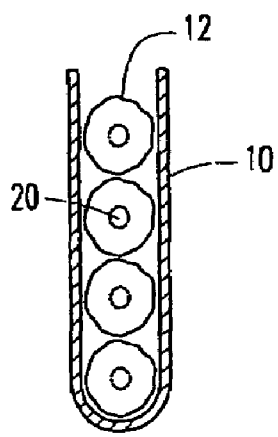
FIG. 1 is a cross-sectional diagram of a tube for holding seeds to be cored.

Reference is now made to FIG. 1 wherein there is shown a cross-sectional diagram of a tube 10 for holding seeds 12 to be cored. The tube 10 is of a common, commercial size and shape suitable for containing at least one, and more preferably more than one, seed 12. In a preferred implementation for use in coring soybeans, the tube 10 is a 5 mL polypropylene culture tube having dimensions of 12 mm by 75 mm that may contain up to eight (hydrated) soybeans (four seeds are shown illustrated). Such a tube 10 may be obtained from VWR International (Catalog No. 60818-383 or 60818-430).

Figure 2A:
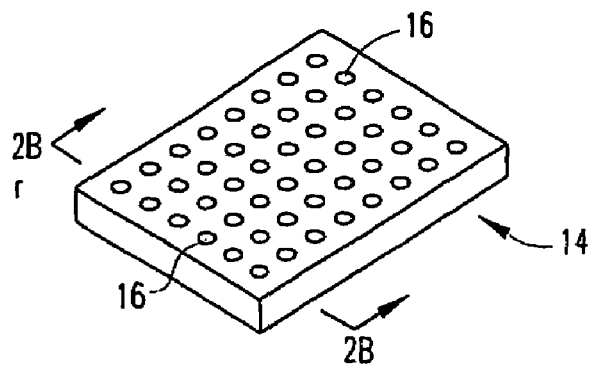
FIGS. 2A and 2B are views (perspective and cross-sectional, respectively) of a tube holding block.
Figure 2B:
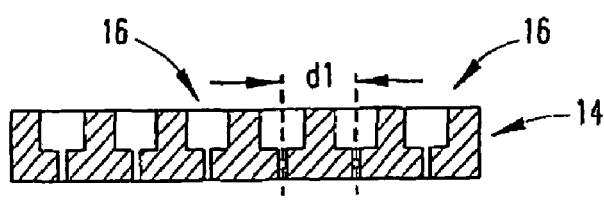

Reference is now made to FIGS. 2A and 2B wherein there are shown views (perspective and cross-sectional, respectively) of a block 14 for holding tubes 10. The block 14 is sized (in width and length) to hold a plurality of tubes 10 in a corresponding plurality of openings 16 formed in a top surface of the block. Any number of openings 16 may be provided in the block 14 as needed. In a preferred embodiment of the present invention, the number of openings 16 may correspond to the number of simultaneous coring operations to be performed. In a more preferred embodiment, the number of openings 16 is an integer multiple (for example, two) of the number of simultaneous coring operations to be performed. The block 14 may be manufactured from any suitable synthetic material, for example, high density polyethylene.

Figure 3:
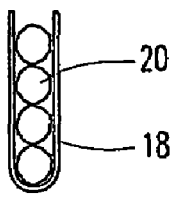
FIG. 3 is a cross-sectional diagram of a tube 18 for holding cores 20 taken from seeds.

Reference is now made to FIG. 3 wherein there is shown a cross-sectional diagram of a tube 18 for holding cores 20 taken from seeds 12. The tube 18 is of a common, commercial size and shape suitable for containing at least one, and more preferably more than one, core 20. In a preferred implementation for use in coring soybeans, the tube 18 is a 1.4 mL polypropylene sample tube that may contain up to eight extracted soybean cores (four are shown illustrated). Such a tube 18 may be obtained from VWR International (Catalog No. 77776-010).

Figure 4A:
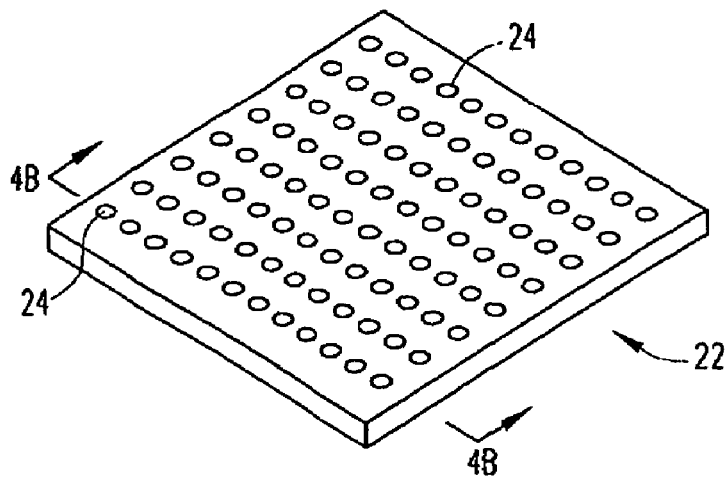
FIGS. 4A and 4B are views (perspective and cross-sectional, respectively) of a well rack for holding tubes.
Figure 4B:
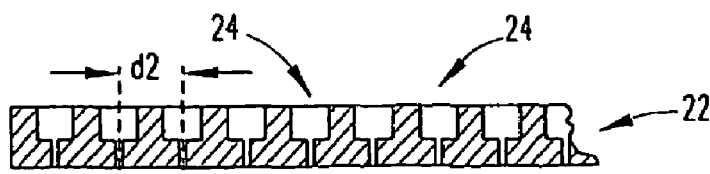

Reference is now made to FIGS. 4A and 4B wherein there are shown views (perspective and cross-sectional, respectively) of a well rack 22 for holding tubes 18. The well rack 22 is sized (in width and length) to hold a plurality of tubes 18 in a corresponding plurality of openings 24 formed in a top surface thereof. Any number of openings 24 may be provided in the well rack 22 as needed. In a preferred embodiment of the present invention, the number of openings 24 may correspond to the number of simultaneous coring operations to be performed. The well rack may be obtained from a number of commercial sources including VWR International (Catalog No. 77776-000) and Matrix (Catalog No. 225-MA).

Reference is now made in combination to FIGS. 2A, 2B, 4A and 4B. The inter-opening spacing (d1) between the openings 16 is chosen during the manufacture of the block 14 to allow for ease of manipulation of the plurality of tubes 10 within a reasonably sized block 14. Additionally, and perhaps more importantly, the inter-opening spacing (d1) is chosen during manufacture of the block 14 in a particular relation to the inter-opening spacing (d2) between the openings 24 in the selected, commercially available, well rack 22. The relationship between the inter-opening spacing (d1) and the inter-opening spacing (d2) is particularly chosen such that the spacing d1 is an integer multiple of the spacing d2 (for example, two). By choosing such a relationship, a more efficient method (to be described in more detail herein) may be implemented for loading seed cores 20 extracted from the tubes 10 into the tubes 18.

Figure 5:
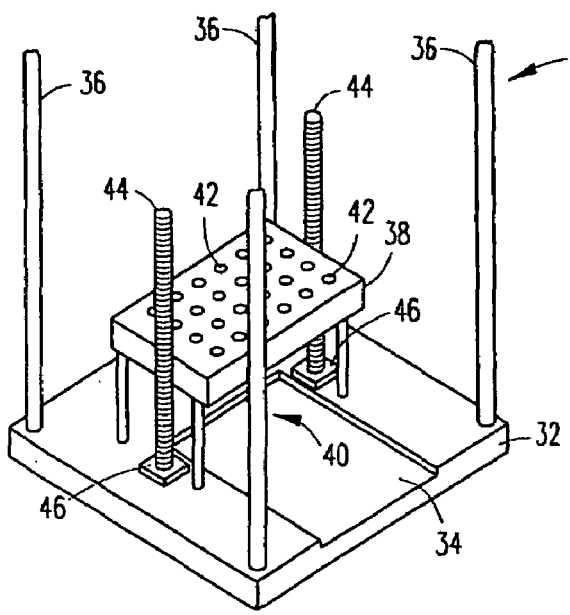
FIG. 5 is an orthogonal view of a base portion of a coring system in accordance with the present invention.

Reference is now made to FIG. 5 wherein there is shown an orthogonal view of a base portion 30 of a coring system in accordance with the present invention. The base portion includes a system supporting base plate 32. A slot 34 is formed in a top surface of the base plate 32 extending inwards from one edge thereof with a size (width and length) at least sufficient to separately receive the well rack 22 (FIG. 4A) and the block 14 in each of a number of positions and/or orientations (as will be described). At about each of the corners of the base plate 32, a slider rod 36 is mounted and extends perpendicularly from the top surface. The function of these slider rods 36 will be explained later in more detail. An alignment block 38 is positioned to lie spaced above and over a back portion 40 of the slot 34. The alignment block 38 includes a plurality of holes 42 arranged in a pattern and spaced apart from each other in a manner that substantially matches at least a fractional portion of (for example, one-half), if not all of, the holes 16 for the block 14 (FIG. 2A). The base portion 30 further includes a pair of threaded rods 44, each rotatably mounted to a tapered bearing 46 that is secured to the top surface of the base plate 32 on opposite sides of the slot 34. The threaded rods 44 extend perpendicularly from the top surface of the base plate 32 in a manner parallel to the slider rods 36.

Figure 6:
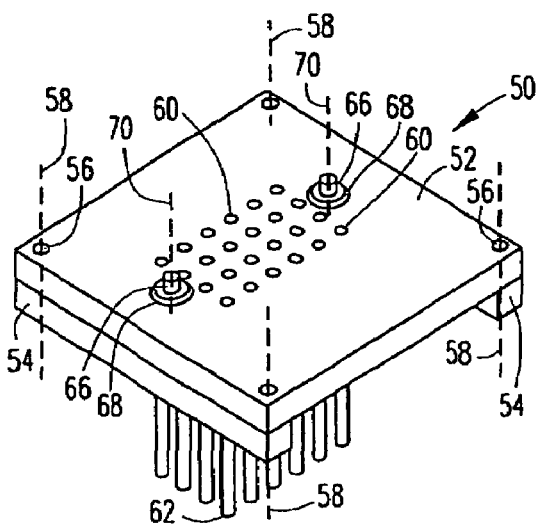
FIG. 6 is an orthogonal view of a coring portion of the coring system in accordance with the present invention.
Figure 7:
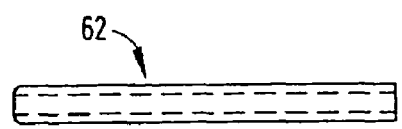
FIG. 7 is a side view of a coring tube.

Reference is now made to FIG. 6 wherein there is shown an orthogonal view of a coring portion 50 of the coring system in accordance with the present invention. The coring portion 50 includes a coring plate 52 mounted to an opposed pair of rigidity beams 54. The rigidity beams 54 help strengthen the coring plate 52 and assist in resisting deformation and/or twisting of the plate caused by operation of the system. At about each of the corners of the coring plate 52, an opening 56 is provided perpendicular to the top surface of the plate and extending through the plate and the rigidity beam 54. A low friction collar (not illustrated) is inserted into each of the openings to allow the slider rods 36 (see, FIG. 5; with position shown by dotted lines 58) to pass there-through with minimal frictional resistance. The coring plate 52 includes a plurality of holes 60 arranged in a pattern and spaced apart from each other in a manner that substantially matches the holes 42 in the alignment block 38 (FIG. 5). In this way, the holes 60, like the holes 42, are arranged in a pattern and spaced apart from each other in a manner that substantially matches at least a fractional portion of (for example, one-half), if not all of, the holes 16 for the block 14 (FIG. 2A). Inserted into, and secured within, each of the holes 60 is a cylindrical, hollow, coring tube 62 (shown also in FIG. 7 having a sharpened end 64) whose inner diameter is sized to be slightly larger than an expected size of the cores 20 of the seeds 12 (see, FIGS. 1 and 3). The tubes 62 extend away from a bottom surface of the coring plate 52. Mounted to the top surface of the coring plate 52 on opposite sides of the pattern of holes 60 is a pair of threaded power nuts 66 that are secured using a corresponding pair of mounting flanges 68. The power nuts 66 are centered over a pair of openings (not explicitly illustrated) that are provide perpendicular to the top surface of the plate 52 and extend there-through. The holes for the power nuts 66 are positioned for alignment with the location of the threaded rods 44 (see, FIG. 5; with position shown by dotted lines 70) to allow passage there-through and further to allow the threads of the rods 44 to engage the threads of the nuts 66.

Figure 8:
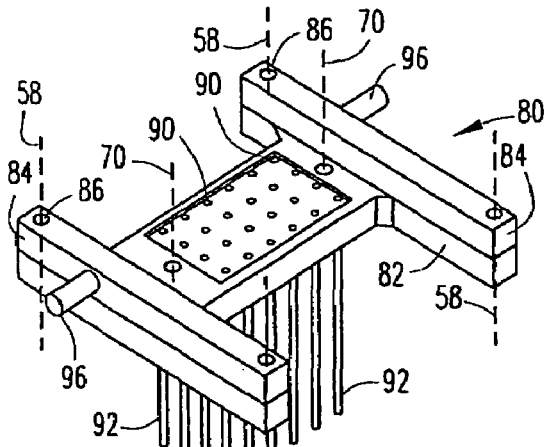
FIG. 8 is an orthogonal view of an extraction portion of the coring system in accordance with the present invention.
Figure 9:
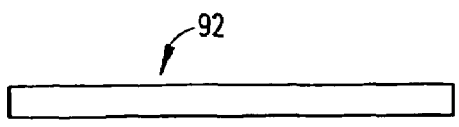
FIG. 9 is a side view of an extraction pin.

Reference is now made to FIG. 8 wherein there is shown an orthogonal view of an extraction portion 80 of the coring system in accordance with the present invention. The extraction portion 80 includes an extraction plate 82 mounted to an opposed pair of rigidity beams 84. The rigidity beams 84 help strengthen the extraction plate 82 and assist in resisting deformation and/or twisting of the plate caused by operation of the system. At about each of the corners of the extraction plate 82, an opening 86 is provided perpendicular to the top surface of the plate and extending through the plate and the rigidity beam 84. A low friction collar (not illustrated) is inserted into each of the openings to allow the slider rods 36 (see, FIG. 5; with position shown by dotted lines 58) to pass there-through with minimal frictional resistance. The extraction plate 82 includes a plurality of holes 90 arranged in a pattern and spaced apart from each other in a manner that substantially matches the holes 42 in the alignment block 38 (FIG. 5) and the holes 60 in the coring plate 52. In this way, the holes 90, like the holes 42 and 60, are arranged in a pattern and spaced apart from each other in a manner that substantially matches at least a fractional portion of (for example, one-half), if not all of, the holes 16 for the block 14 (FIG. 2A). Inserted into, and secured within, each of the holes 90 is a cylindrical extraction pin 92 (shown also in FIG. 9) whose outer diameter is sized to be slightly smaller than the inner diameter of the coring tube 62 (FIG. 7) and generally about the expected size of the cores 20 of the seeds 12 (see, FIGS. 1 and 3). The pins 92 extend away from a bottom surface of the extraction plate 82. The extraction plate 82 further includes a pair of openings 94 (one explicitly illustrated) provided perpendicular to the top surface of the plate and extending there-through, and positioned for alignment with the location of the threaded rods 44 (see, FIG. 5; with position shown by dotted lines 70) to allow free passage there-through. The extraction portion 80 further includes a pair of opposed control handles 96 mounted to the rigidity beams 84.

Figure 10:
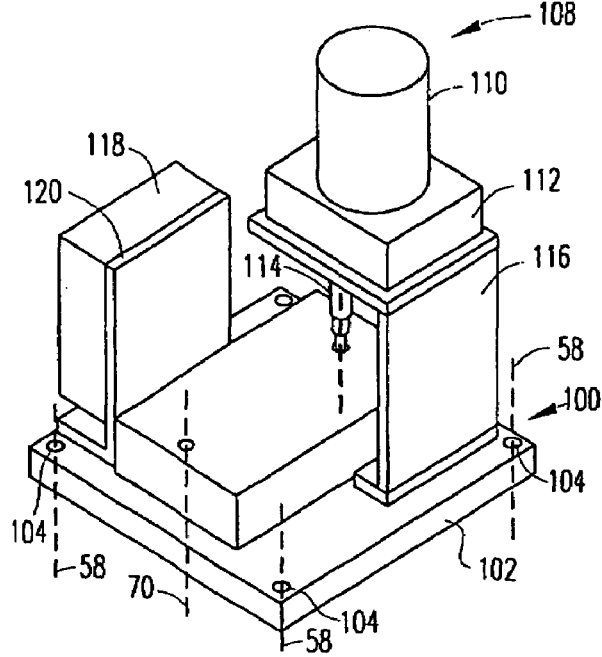
FIG. 10 is an orthogonal view of a drive portion of the coring system in accordance with the present invention.

Reference is now made to FIG. 10 wherein there is shown an orthogonal view of a drive portion 100 of the coring system in accordance with the present invention. The drive portion 100 includes a cap plate 102. At about each of the corners of the cap plate 82, an opening 104 is provided perpendicular to the top surface of the plate and extending through the plate. An appropriate fastening device (such as, for example, a nut, clip or collar) is inserted into each of the openings 104 for mounting the cap plate 102 to the slider rods 36 (see, FIG. 5; with position shown by dotted lines 58). The cap plate 102 further includes a pair of openings (not explicitly illustrated) provided perpendicular to the top surface of the plate and extending there-through, and positioned for alignment with the location of the threaded rods 44 (see, FIG. 5; with position shown by dotted lines 70) to allow passage there-through using a pair of tapered bearings (not explicitly shown).

Figure 11:
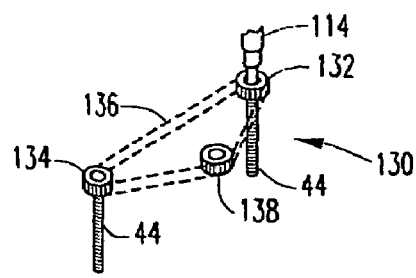
FIG. 11 is an illustration of a belt/pulley drive train used within the drive portion.

Reference is now additionally made to FIG. 11. Within an enclosure 106, the drive portion 100 includes a belt/pulley drive train 130 that connects to the pair of threaded rods 44 and when driven in a manner to be described causes the threaded rods to similarly rotate in either direction. The belt/pulley drive train 130 includes a pair of drive pulleys 132 and 134, a tensioning pulley 138 and a belt (for example, a timing belt) 136. The first drive pulley 132 is configured for connection to one of the threaded rods 44. The second drive pulley 134 is configured for connection to the other threaded rod 44. The two pulleys 132 and 134 are connected to each other using a drive belt 136 that wraps around the two pulleys 132 and 134 as well as the tensioning pulley 138. The position of the tensioning pulley 138 may be adjusted to control the tension applied to the belt 136.

Actuation of the belt/pulley drive train 130 is made by a motor system 108 comprising a motor 110 and a gear reduction drive 112 operable to rotate a shaft 114 that is connected to the first drive pulley 132. Through the belt 136, the rotation causes a corresponding (in both direction and speed) rotation in the second drive pulley 134. The motor system 108 is mounted to the cap plate 102 using a bracket 116. A control box 118 is mounted to the cap plate using bracket 120 and encloses the electronic control components required to control the actuation of the motor 110 and the operation of the drive portion 108 of the system.

Reference is now made to FIG. 12 wherein there is shown an exploded orthogonal view of the coring system of the present invention. This illustration shows how the FIG. 5 base portion 30, FIG. 6 coring portion 50, FIG. 8 extraction portion 80 and FIG. 10 drive portion 100 are assembled together to form the coring system of the present invention. A view of the coring system, as assembled, is shown in FIG. 13. In assembling the coring system it is important that proper alignment is maintained between all of the included portions. For example, the coring portion 50 and base portion 30 must be carefully aligned to ensure that the coring tubes 62 are aligned with and will pass through the openings 42 in the alignment block 38. Additionally, the extraction portion 80 and coring portion 50 must be carefully aligned to ensure that the extraction pins 92 are aligned with and will pass through the openings in the coring tubes 62. Still further, the drive portion 100 must be aligned with the threaded rods 44 to ensure that the pulleys 132 and 134 are properly positioned to engage the rods for actuation. The slider rods 36 are important components in effectuating the alignment necessary to ensure proper assembly and operation of the coring system.

To restrict the downward movement of the coring portion 50, a pair of stops 120 are mounted to the bottom surface of the coring plate. As the coring portion 50 moves down, the stops 120 eventually contact the top surface of the base plate 32 and terminate further downward movement. These stops 120 have a length selectively chosen to terminate downward movement of the coring portion 50 at a point just at or slightly after where the coring tubes 62 have completed their coring operation and just before where the tubes may become damaged. To restrict the upward movement of the extraction portion 80, a set of collar stops 122 are mounted to the slider rods 36. As the extraction portion 80 moves up, the rigidity beams 84 eventually contact the stops 122 and terminate further upward movement. The position of the stops 122 on the rods 36 is selectively chosen to terminate upward movement of the extraction portion 80 at a point where the pins 92 have been completely withdrawn from the coring tubes 62. Upward movement of the coring portion 50 and downward movement of the extraction portion 80 is restricted by the interaction between these two portions. In this regard, a pinch point may be formed between the extraction plate 82 and coring plate 52 during some operational steps of the coring system. Appropriate precautionary steps must be taken to guard against operator injury at the pinch point.

It will be noted that movement of the coring portion 50 is effectuated through the use of the drive portion 100, threaded rods 44 and power nuts 66. More specifically, when the drive portion 100 is actuated and the two threaded rods 44 are simultaneously rotated in a counter-clockwise direction, the coring portion 50 moves downward and will continue to so move until the drive portion is deactivated or the stops 120 contact the base plate 32. Conversely, when the drive portion 100 is actuated and the two threaded rods 44 are simultaneously rotated in a clockwise direction, the coring portion 50 moves upward and will continue to so move until the drive portion is deactivated or the coring portion contacts the extraction portion 80 and pushes the extraction portion into contact with the stops 122.

Movement of the extraction portion 80, however, is effectuated manually by the system operator using the handles 96. More specifically, downward movement of the extraction portion 80 occurs responsive to downward pushing on the handles 96 and is terminated when the pushing stops or the extraction portion contacts the coring portion 50. Upward movement of the extraction portion 80, on the other hand, occurs responsive to upward pulling on the handles 96 and is terminated when the pulling stops or the extraction portion contacts the collar stops 122.

To assist the system operator in the manual manipulation of the extraction portion, a counterweight system 124 is utilized. A weight (not shown) is connected by a cable (also not shown) to the extraction portion 80. A pulley (also not shown) is mounted to a bottom side of the drive plate 102 and the cable is threaded over the pulley. The weight is contained within a vertical tube 126 and moves up and down with corresponding down and up movement of the extraction portion 80.

Although a preferred embodiment of the coring system utilizes a mechanical drive for the coring portion 50 and a manual drive for the extraction portion 80, it will be understood that the entire coring system (i.e., both the coring portion 50 and the extraction portion 80) may be manually driven or motor driven utilizing the counterweight and screw drive technologies described herein.

Figures 14A, 14B, 14C:
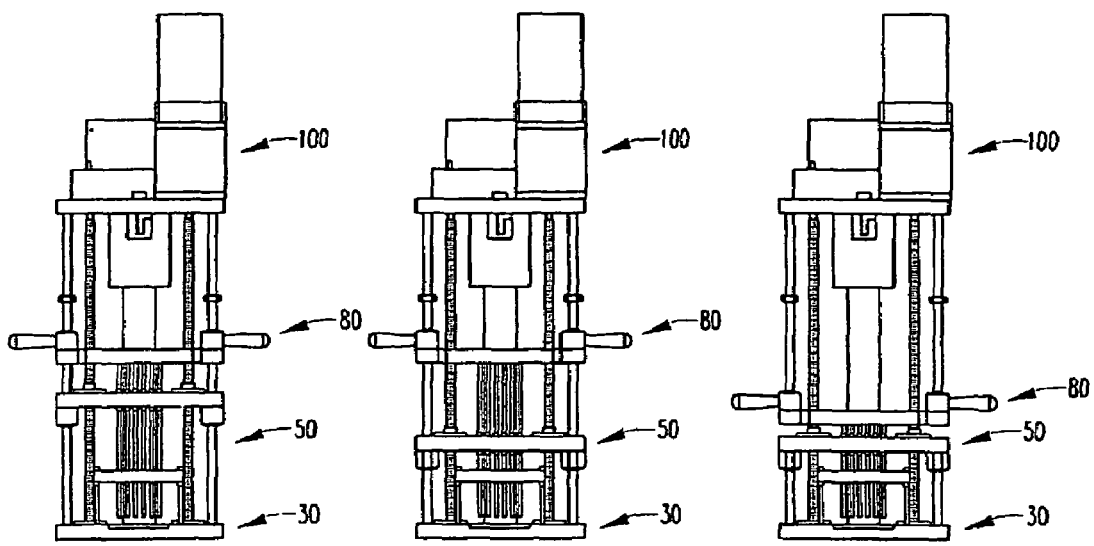
FIGS. 14A-14C are side views of the coring system of the present invention sequentially illustrating its operation.

Reference is now made to FIGS. 14A-14C wherein there are shown side views of the coring system of the present invention sequentially illustrating its operation. In FIG. 14A, the coring system is shown in a starting position. At this point, the coring portion 50 is raised sufficiently enough to allow for a block 14 holding tubes 10 filled with seeds 12 (not shown, see, FIGS. 1 and 2A) to be inserted into the slot 34 and positioned in the back portion 40 thereof such that the tubes 10 are placed under the openings 42 in the alignment block 38. The drive portion 100 is then activated to move the coring portion 50 downward as shown in FIG. 14B. At this position, the coring tubes 62 have entered the tubes 10 in the block 14 and cored the contained seeds 12. Following completion of the coring action, the drive portion 100 is again actuated, this time to move the coring portion 50 upward to a position as shown in FIG. 14A. With this movement, the extracted cores 20 of the seeds 12 remain contained with the coring tubes 62. The block 14 holding tubes 10 may then be removed from the slot 34 and replaced with a well rack 22 holding tubes 18 (not shown, see, FIGS. 3 and 4A). The well rack 22 is inserted into the slot 34 and positioned in the back portion 40 thereof such that the tubes 18 are placed under the openings 42 in the alignment block 38. Now, the drive portion 100 is then activated to move the coring portion 50 downward as shown in FIG. 14B. At this position, the coring tubes 62 are located just over certain ones of the tubes 18. The operator then manually pushes the extraction portion 80 down to a position as shown in FIG. 14C (one or more times may be required). With this pushing movement, the extraction pins 92 enter the coring tubes 62 and push the contained cores 20 therefrom for deposit in the tubes 18 of the well rack 22. The extraction portion 80 is then manually pulled upward back to a position as shown in FIG. 14B. Next, the drive portion 100 is again actuated to return the coring portion 50 upward to a position as shown in FIG. 14A. The rack 22 holding the tubes 18 may then be removed from the slot 34, and replaced with a new block 14 holding tubes 10. The entire process may then be repeated to extract and deposit a next set of cores 20.

If the number of openings 16 (for block 14) and number of openings 24 (for rack 22) are equal, and further if that number equals the number of coring tubes 62 provided by the machine, then the operation to core seeds and fill the well rack 22 may be performed in two steps (i.e., a first coring step using the coring portion 50 followed by a second depositing step using the extraction portion 80). In such a case, it is quite easy to track samples from their block 14 position to their position in the well rack 22 because there is a direct mapped relationship from a single block to a corresponding single rack. For number of reasons, however, a more likely scenario exists where the number of coring tubes 62 is smaller than the number of openings 24 in the well rack 22. When this occurs, it is a much more difficult task to track samples from their block 14 position to their position in the well rack 22 because multiple blocks are needed to fill a single rack. The configuration and operation of the coring system of the present invention, however, addresses this issue by providing a controlled and coordinated operation that allows for accurate mapping of samples from their source tube 10 the destination tube 18.

Figure 15:
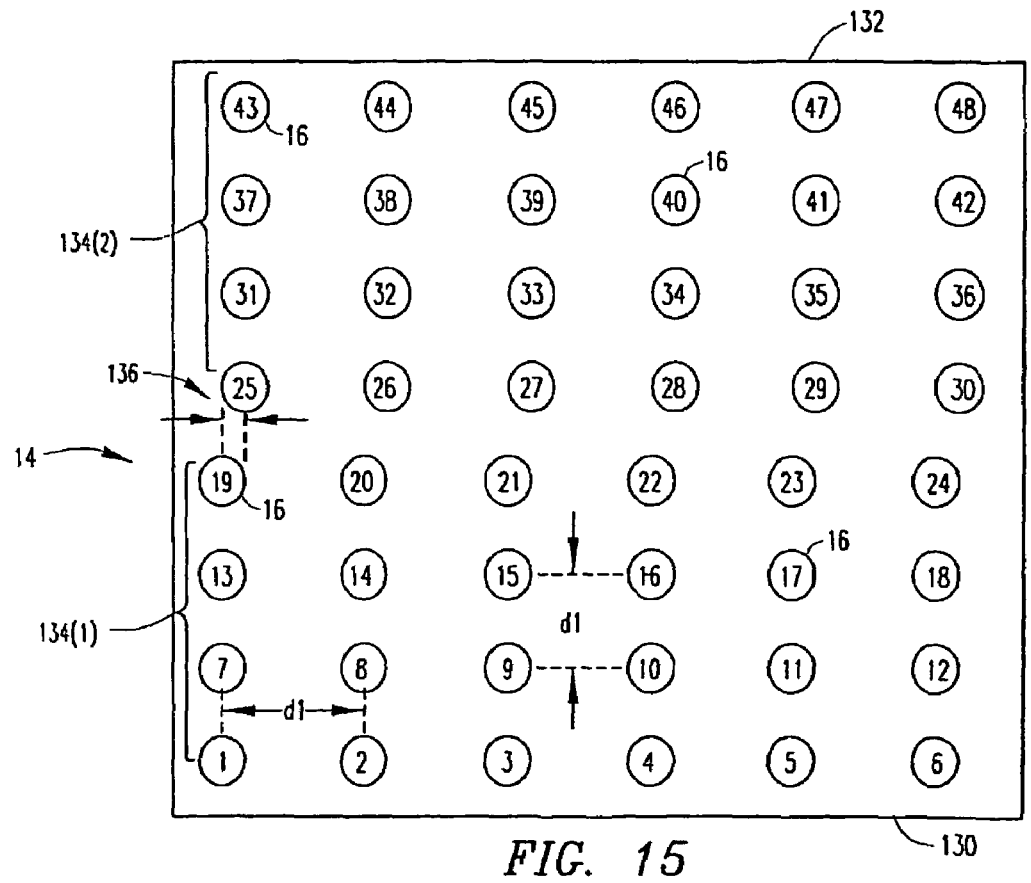
FIG. 15 is a top view of an exemplary block like that shown in FIGS. 2A and 2B.

Reference is now made to FIG. 15 wherein there is shown a top view of an exemplary block 14. The block 14 includes openings 16 arranged in a 6×8 array (thus providing a total of 48 openings for holding tubes 10). The block 14 has a first edge 130 and a second edge 132 (that are opposed with respect to each other). In the coring system, the coring portion 50 is provided with an arrayed 6×4 set of coring tubes 62. The distance between adjacent coring tubes 62 (either horizontally or vertically) is set equal to d1, which is also the distance between adjacent openings 16 in the block 14. Although not required, the 6×8 openings 16 may be physically divided into two 6×4 groups 134. To assist in identifying and tracking the groups 134 on the block 14, the groups may be offset slightly from each other (as shown at reference 136).

When the block 14 is inserted into the slot 34 of the coring system with the first edge 130 toward the back portion 40, the subsequent coring operation will core the seeds contained in tubes 10 that are located in a first one of the groups 134(1). Thus, samples 1-24 of this block 14 are obtained with this first coring operation. Conversely, when the block is turned around and inserted into the slot 34 of the coring system with the second edge 132 toward the back portion 40, the subsequent coring operation will core the seeds contained in tubes 10 that are located in a second one of the groups 134(2). Thus, samples 25-48 of the same block 14 are obtained with this second coring operation. It will, however, be recognized that the order with which the individual samples are obtained is opposite in that the first operation with reference to the left corner of first edge 130 collects samples 1-24, while the second operation with reference to left corner of second edge 132 collects samples 48-25.

Figures 16, 17:
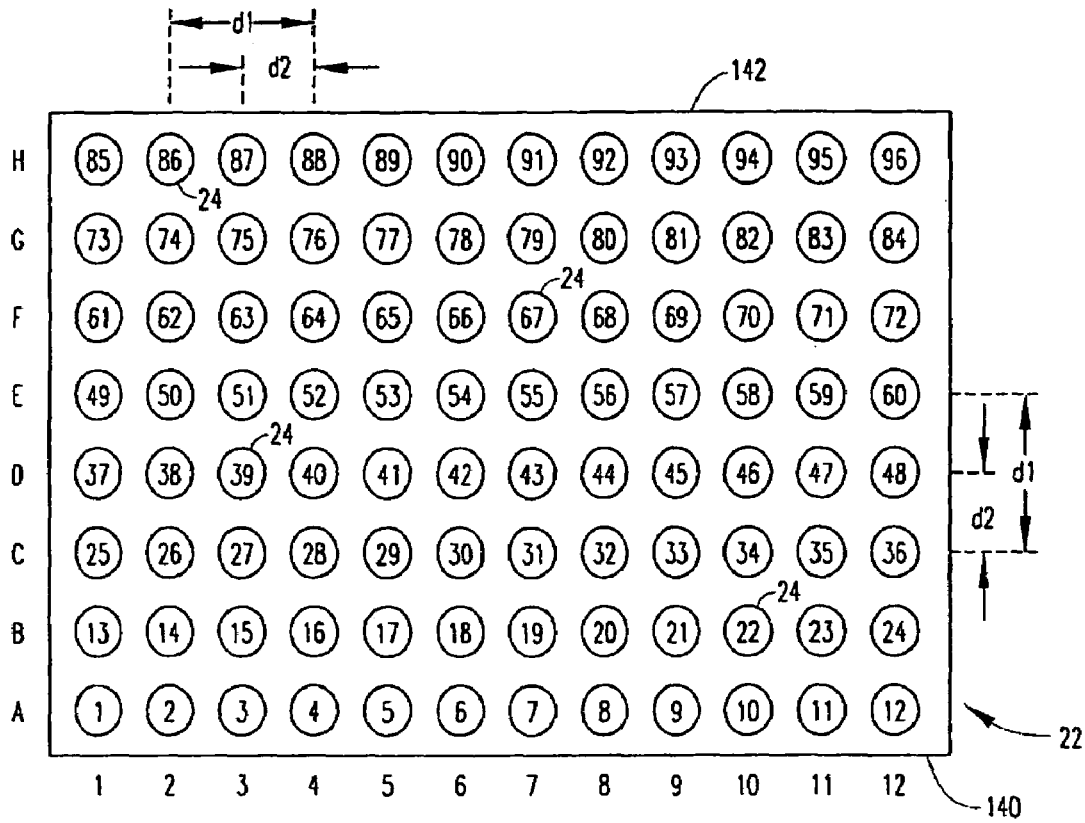
FIG. 16 is a top view of an exemplary well rack like that shown in FIGS. 4A and 4B.
FIG. 17 is a table mapping sample locations from two source blocks to a single well rack.

Reference is now made to FIG. 16 wherein there is shown a top view of an exemplary well rack 22. The rack 22 includes openings 24 arranged in a 12×8 array (thus providing a total of 96 openings for holding tubes 18). The rack 22 has a first edge 140 and a second edge 142 (that are opposed with respect to each other). In the coring system, the coring portion 50 is provided with an arrayed 6×4 set of coring tubes 62. The distance between adjacent coring tubes 62 (either horizontally or vertically) is set equal to d1, however the distance between adjacent openings 24 in the rack 22 is set equal to d2, wherein d1 is an integer multiple (in this case, two) of d2.

Filling of a rack 22 with sampled cores 20 occurs as follows. First, with respect to a first block 14, a coring operation on the first group 134(1) is performed. The first block 14 is then removed and saved. The rack 22 is then inserted into the slot 34 of the coring system with the first edge 140 toward the back portion 40, and it is aligned with the alignment block 38 (in a first position) such that its openings 42 are aligned with a first sub-set of openings 24 located at the intersection points of the odd numbered columns (1, 3, 5, 7, 9, 11) and the rows labeled A, C, E and G. The subsequent extraction operation then deposits the cores 20 contained in the coring tubes 62 into the non-consecutive sample tubes 18 at the first sub-set of openings 24. The rack 22 is then removed and saved, and the first block 14 is then returned to the coring system (with an opposite orientation) for performance of a coring operation on the second group 134(2). The first block 14 is then removed. The rack 22 is then returned to the slot 34 of the coring system with the first edge 140 toward the back portion 40, and it is aligned with the alignment block 38 (in a second position) such that the openings 42 are aligned with a second sub-set of openings 24 located at the intersection points of the even numbered columns (2, 4, 6, 8, 10, 12) and the rows labeled A, C, E and G. The subsequent extraction operation then deposits the cores 20 contained in the coring tubes 62 into the sample tubes 18 at the second sub-set of openings 24. At this point, one-half of the rack 22 has been filled with cores 20 obtained from a single block 14.

Next, the process described above is repeated with respect to a second block 14 and the rows labeled B, D, F, and H of the rack 22. In repeating, however, the well rack 22 is rotated into an opposite orientation from that used above and inserted into the slot 34 of the coring system with the second edge 142 toward the back portion 40. Thus, cores 20 obtained from the first group 134(1) of tubes 10 are deposited in a third sub-set of non-consecutive openings 24 of the rack 22 located at the intersection points of the odd numbered columns (1, 3, 5, 7, 9, 11) and the rows labeled B, D, F, and H (when the rack is in the first position), and cores 20 obtained from the second group 134(2) of tubes 10 are deposited in a fourth sub-set of non-consecutive openings 24 of the rack 22 located at the intersection points of the even numbered columns (2, 4, 6, 8, 10, 12) and the rows labeled B, D, F and H (when the rack is in the second position). At this point, the entire rack 22 has been filled with cores 20 obtained from two separate blocks 14.

Reference is now made to FIG. 17 wherein there is shown a table mapping sample locations from two source blocks 14 to a single well rack 22. The cores 20 from locations 1-48 of the first block 14 are deposited in the tubes 18 at the openings 24 located at the intersection points of the odd (first orientation, first position) and even (first orientation, second position) numbered columns and the rows labeled A, C, E and G. Next, the cores 20 from locations 1-48 of the second block 14 are deposited in the tubes 18 at the openings 24 located at the intersection points of the odd (second orientation, first position) and even (second orientation, second position) numbered columns and the rows labeled B, D, F and H. To distinguish the locations 1-48 of the two source blocks 14 from each other in the mapped FIG. 17, the locations 1-48 for the first block are denoted by normal-faced type and the locations 1-48 for the second block 14 are denoted by bold-faced type. With the foregoing the following may be observed: by specifying the d1/d2 relationship, as well as the integer multiple relationship between the number of coring tubes 62, openings 14 and openings 24, four core/deposit operations using simple rotations can be used to fill the well rack in a highly organized and regular fashion with minimal risk for error. In this way, the operator can accurately track a core in a certain tube 18 of a well rack 22 to its source block 14 and more particularly its source tube 10 from a certain opening 16.

Although preferred embodiments of the method and apparatus of the present invention have been illustrated in the accompanying Drawings and described in the foregoing Detailed Description, it will be understood that the invention is not limited to the embodiments disclosed, but is capable of numerous rearrangements, modifications and substitutions without departing from the spirit of the invention as set forth and defined by the following claims.

What is claimed is:

1. A coring system for coring a plurality of objects, the coring system comprising:
    a sample plate comprising a plurality of openings arranged in a two-dimensional array, at least one of the openings adapted to receive a plurality of objects;
    a coring plate including a plurality of openings arranged in a two-dimensional array;
    a plurality of coring tubes, each coring tube mounted within one of the plurality of openings in the coring plate; and
    a mechanical drive mechanism for translating the coring plate between a retracted position and an activated position, wherein translation toward the activated position causes the plurality of coring tubes to core the plurality of objects in the sample plate.

2. The system of claim 1 further including:
    an extraction plate including a plurality of openings aligned with the plurality of openings in the coring plate; and
    a plurality of extraction pins, each extraction pin mounted within one of the plurality of openings in the extraction plate and positioned for insertion within an opening of a corresponding coring tube.

3. The system of claim 1 wherein each of the openings of the sample plate are adapted to receive a plurality of objects.

4. The system of claim 1 further including a sample tube adapted to be received within the at least one of the openings of the sample plate for holding the plurality of objects received in the at least one of the openings of the sample plate.

* * * * *